United States Patent [19]

Sundeen et al.

[11] 4,263,293
[45] Apr. 21, 1981

[54] HETEROCYCLIC CONTAINING AMIDES AS INHIBITORS OF MAMMALIAN COLLAGENASE

[75] Inventors: Joseph E. Sundeen, Yardley, Pa.; Tamara Dejneka, Skillman, N.J.

[73] Assignee: E. R. Squibb & Sons, Inc., Princeton, N.J.

[21] Appl. No.: 154,748

[22] Filed: May 30, 1980

[51] Int. Cl.³ ............... A61K 31/535; A61K 31/445; C07D 295/14
[52] U.S. Cl. ............................ 424/248.5; 424/248.52; 424/250; 424/267; 424/274; 544/159; 544/400; 546/233; 546/234; 546/247; 260/326.43
[58] Field of Search ............... 544/159, 400; 546/233, 546/234, 247; 260/326.43; 424/248.5, 248.52, 250, 267, 274

[56] References Cited
U.S. PATENT DOCUMENTS 4,105,776  8/1978  Ondetti et al. ........................ 424/274

FOREIGN PATENT DOCUMENTS 1989  10/1978  European Pat. Off. .

Primary Examiner—Henry R. Jiles
Assistant Examiner—R. W. Ramsuer
Attorney, Agent, or Firm—Lawrence S. Levinson; Donald J. Barrack

[57] ABSTRACT

Mammalian collagenase is inhibited by compounds having the formula

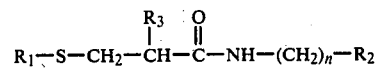

wherein
$R_1$ is hydrogen, alkanoyl of 2 to 10 carbon atoms or arylcarbonyl;
$R_2$ is 1-pyrrolidinyl, 1-piperidinyl, 4-morpholinyl, 1-piperazinyl, or 4-alkyl-1-piperazinyl;
$R_3$ is alkyl of 3 to 8 carbon atoms, cycloalkyl, aryl, or arylalkyl; and
n is an integer of 1 to 20.

10 Claims, No Drawings

HETEROCYCLIC CONTAINING AMIDES AS INHIBITORS OF MAMMALIAN COLLAGENASE

RELATED APPLICATIONS

United States patent application Ser. No. 51,915, filed June 25, 1979 and Ser. No. 121,352, filed Feb. 14, 1980 disclose mammalian collagenase inhibitors having the formula $$R_a-S-CH_2-\underset{\underset{(CH_3)_2-CH-CH_2}{|}}{CH}-\overset{O}{\overset{\|}{C}}-P_b,$$

wherein $R_a$ is hydrogen or alkanoyl of 2 to 10 carbon atoms; $R_b$ is hydroxy, amino or $$-NH-(CH_2)_m-\underset{\underset{R_c}{|}}{CH}-\overset{O}{\overset{\|}{C}}-R_d;$$

$R_c$ is hydrogen, alkyl of 1 to 4 carbon atoms, $$-(CH_2)_3-NH\overset{NH}{\overset{\|}{C}}NH_2, \text{ or } -(CH_2)_2-\overset{O}{\overset{\|}{C}}-NH_2;$$

$R_d$ is hydroxy, amino, arginine, leucine, glutamine, alanine or glycine; and m is 0 or an integer of 1 to 9.

BACKGROUND OF THE INVENTION

European Patent Application No. 1,989, published May 30, 1979, discloses compounds having the formula $$R_e-S-\underset{\underset{(O)_m}{\downarrow}}{(C)_n}-\overset{O}{\overset{\|}{C}}-NR_hR_i,$$
(with $R_f$, $R_g$ substituents)

wherein the symbols are, inter alia, as follows: $R_e$ is hydrogen, m is 0, $R_f$ and $R_g$ are hydrogen, alkyl, cycloalkyl, arylalkyl, or aryl, $R_h$ and $R_i$ are hydrogen, aminoalkyl, alkylaminoalkyl, dialkylaminoalkyl, phenylaminoalkyl, diphenylaminoalkyl, (phenyl)(alkyl)aminoalkyl, or heterocyclic and n is 1 to 17. The compounds are disclosed as useful for the treatment of diseases characterized or complicated by an imbalance of immune hemostasis. The treatment of rheumatoid arthritis is specifically disclosed.

BRIEF DESCRIPTION OF THE INVENTION

Mammalian collagenase is inhibited by compounds having the formula $$R_1-S-CH_2-\underset{\underset{R_3}{|}}{\overset{*}{CH}}-\overset{O}{\overset{\|}{C}}-NH-(CH_2)_n-R_2. \qquad I$$

In formula I, and throughout the specification, the symbols are as defined below.

$R_1$ is hydrogen, alkanoyl of 2 to 10 carbon atoms (acetyl is preferred) or arylcarbonyl (benzoyl is preferred);

$R_2$ is 1-pyrrolidinyl, 1-piperidinyl, 4-morpholinyl, 1-piperazinyl, or 4-alkyl-1-piperazinyl;

$R_3$ is alkyl of 3 to 8 carbon atoms, cycloalkyl of 3 to 7 carbon atoms, aryl, or arylalkyl; and n is an integer of 1 to 20.

The term "aryl", as used throughout the specification, either individually or as part of a larger group, refers to phenyl or phenyl substituted with one, two or three alkyl, alkoxy, halogen, amino, hydroxy, or alkanoyloxy groups. Phenyl and monosubstituted phenyl are the preferred aryl groups.

The terms "alkyl" and "alkoxy", as used throughout the specification (unless otherwise defined), either individually or as part of a larger group, refer to groups having 1 to 8 carbon atoms.

The term halogen, as used throughout the specification, either individually or as part of a larger group, refers to fluorine, chlorine, bromine and iodine.

DETAILED DESCRIPTION OF THE INVENTION

The compounds of this invention can be prepared using as a starting material a carboxylic acid having the formula $$HO-CH_2-\underset{\underset{R_3}{|}}{CH}-\overset{O}{\overset{\|}{C}}-OH. \qquad II$$

Heating a carboxylic acid of formula II with phosphonic acid yields a compound having the formula $$CH_2=\underset{\underset{R_3}{|}}{C}-\overset{O}{\overset{\|}{C}}-OH, \qquad III$$

which can in turn be reacted with a thio acid having the formula $$R_1'-SH, \qquad (IV)$$

wherein $R_1'$ is alkanoyl of 2 to 10 carbon atoms or arylcarbonyl, to yield a product having the formula $$R_1'-S-CH_2-\underset{\underset{R_3}{|}}{CH}-\overset{O}{\overset{\|}{C}}-OH. \qquad V$$

An acid of formula V can be coupled with an aminoalkyleneheterocyclic having the formula $$NH_2-(CH_2)_n-R_2 \qquad (VI)$$

to yield the compounds of formula I wherein $R_1$ is other than hydrogen. The coupling reaction can be effected by first activating the acid of formula V, e.g., by formation of a mixed or symmetrical anhydride, acid chloride, or active ester, or by the use of Woodward reagent K, EEDQ (N-ethoxycarbonyl-2-ethoxy-1,2-dihydroxyquinoline) or the like. A preferred method of activation comprises first treating an acid of formula V with an organic base (e.g., triethylamine) and then adding ethyl chloroformate.

Those products of formula I wherein $R_1$ is hydrogen can be prepared from corresponding compounds of formula I wherein $R_1$ is alkanoyl or arylcarbonyl by treatment of the acylthio compound with concentrated ammonium hydroxide.

Alternatively, the compounds of this invention can be prepared using as a starting material a malonic acid ester derivative having the formula

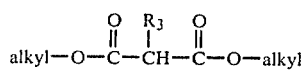
                                                                VII

Hydrolysis of a malonic acid ester derivative of formula VII yields the corresponding compound having the formula

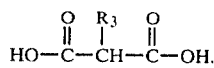
                                                                VIII

Sequential reaction of a diacid of formula VIII with a secondary amine (such as dimethylamine) and formaldehyde yields the corresponding compound having the formula

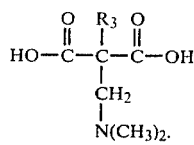
                                                                IX

Conversion of a compound of formula IX to the corresponding compound having the formula

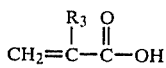
                                                                III can be accomplished by melting the precursor compound. The compounds of this invention can be prepared from the compounds of formula III using the procedures described above.

The compounds of formula I have at least one asymmetric carbon atom; the carbon noted with an asterisk (*) in formula I. The compounds accordingly exist in stereomeric forms or as racemic mixtures thereof. All of these are within the scope of this invention. The above described synthesis can utilize the starting compounds in the form of a racemic mixture or as a stereomer.

In mammals, collagenase is one of the key enzymes involved in the cartilage and joint destruction of rheumatoid arthritis; see, for example, *Arthritis and Rheumatism*, 20 (6):1231 (1977). It is, therefore, desirable to inhibit the action of the collagenase enzyme.

While not limiting the scope of this invention to a specific theory or mechanism of operation, it is nevertheless helpful to an understanding of the invention to review the possible reasons for the activity of the compounds of formula I. The main components of cartilage are the collagen polypeptide molecules. These polypeptides are cleaved by mammalian collagenase at a single site. The compounds of this invention resemble the susceptible sequence of the collagen molecules and, it is theorized, bind to the mammalian collagenase enzyme and inhibit its activity.

The mammalian collagenase enzyme contains zinc, which assists in the cleavage of the glycine-leucine or a glycine-isoleucine bond and contains an extended cleft which interacts with an extended portion of the collagen molecule. This molecule in turn contains arginine as the last homologous amino acid in the substrate sequence adjacent to the cleavage site, a sequence showing a high degree of homology among the various types of collagen molecules. The inhibitors of this invention make use of these features of the enzyme and make modifications to enhance binding to the mammalian collagenase molecule.

The action of mammalian collagenase has also been implicated as a causative factor in several other diseases in mammals. These diseases include periodontal disease, corneal ulceration, tumor invasiveness, and epidermolysis bullosa; see, for example, *American Journal of Pathology*, 92 (2):509 (1978) and *The New England Journal of Medicine*, 291 (13):652 (1974).

For use in the treatment of rheumatoid arthritis, the compounds of this invention can be administered to a mammal in need thereof either orally or by injection intraarticularly into the affected joint. The daily dosage for a 70 kilogram mammal will be in the range of about 10 milligrams to 1 gram.

The compounds of this invention can be formulated in compositions such as tablets, capsules or elixirs for oral administration or in sterile solutions or suspensions for parenteral administration. About 10 to 500 mg of a compound of formula I or physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein $R_3$ is 2-methylpropyl are preferred. Also preferred are those compounds of formula I wherein $R_1$ is hydrogen, acetyl or benzoyl. Also preferred are those compounds of formula I wherein n is 2, 3 or 4.

The following examples are specific embodiments of this invention.

EXAMPLE 1

(±)-2-[(Acetylthio)methyl]-4-methyl-N-[2-(4-morpholinyl)ethyl]pentanamide (A) 4-Methyl-2-methylenepentanoic acid

Method I (i) Isocaproic Acid

Potassium cyanide (28 g) is partly dissolved in 125 ml of ethanol and 30 ml of water. Amyl bromide (63.6 g) is added and the reaction mixture is digested on the steam cone for 24 hours. The solution is decanted from the potassium bromide on to 35 g of potassium hydroxide. This is digested on the steam cone for 20 hours, diluted with 50 ml of water and concentrated in vacuo to remove the ethanol. A 1:1 mixture of sulfuric acid and water is added to the reaction mixture and product is extracted with petroleum ether to yield 60.6 g of crude product. Vacuum distillation yields 43.4 g of product boiling at 90°-98° C./9 mm of Hg.

(ii) 2-(Hydroxymethyl)-4-methylpentanoic acid

Diisopropylamine (20.6 g) is dissolved in 80 ml of dry tetrahydrofuran. This solution is cooled to −30° C. n-Butyllithium (77 ml of 2.6 M in hexane) is added dropwise in a nitrogen atmosphere at a rate that maintains the reaction at −30° to −20° C. This solution is stirred at −20° C. for 30 minutes. Isocaproic acid (11.6 g) in 10 ml of tetrahydrofuran is added dropwise at −20° to −10° C., then stirred at −10° C. for 30 minutes. In a separate flask, paraformaldehyde (28 g) is heated to about 200° C. and the vapors are carried in a stream of nitrogen over the surface of the tetrahydrofuran solution of the dilithium salt of isocaproic acid. During this procedure the temperature is kept between −10° and +10° C. After all of the paraformaldehyde has vaporized the reaction mixture is cooled to 0° C. and 10% hydrochloric acid is added dropwise until the reaction mixture becomes acidic. Product is extracted with 2 portions of ether (400 ml each). The ether is dried with magnesium sulfate, filtered and concentrated in vacuo to yield 13.2 g of crude material. Product is vacuum distilled to yield 9.0 g, boiling point 135°–142° C./9 mm of Hg.

(iii) 4-Methyl-2-methylenepentanoic acid 2-(Hydroxymethyl)-4-methylpentanoic acid (8.7 g) is heated with 10 drops of 85% phosphonic acid in a Wood's metal bath at 220° C. for 20 minutes. A distillation head is attached and the pressure is slowly decreased to 60 mm while the temperature is increased to 270° C. Product starts to distill and the pressure is further decreased to 10 mm. The vapor temperature varies between 180° and 190° C. The yield of the title compound as distillate is 7.0 g.

Method II (i) 2-Carboxy-4-methylpentanoic acid

A solution of 91.1 g of 2-(ethyloxycarbonyl)-4-methylpentanoic acid, ethyl ester in 300 ml of methanol is treated for 6 hours at 80° C. with 400 ml of 10% sodium hydroxide. The solution is concentrated in vacuo to 400 ml and acidified with 10% hydrochloric acid. The product is extracted with ethyl acetate to yield 67.6 g of the title compound, which crystallizes on standing. Recrystallization from ethyl acetate-hexane yields the title compound, melting point 102°–105° C.

(ii) 2-Carboxy-4-methyl-2-[(dimethylamino)methyl]pentanoic acid

2-Carboxy-4-methylpentanoic acid (67 g) is suspended in 400 ml of water and cooled to 5° C. Aqueous 40% dimethylamine (50 g) is added to the suspension followed by aqueous 37% formaldehyde (35.7 g). The resulting solution is stirred for about 16 hours and solid product is filtered and dried in vacuo to yield 57.3 g of the title compound, melting point 134°–137° C. with carbon dioxide and dimethylamine given off.

(iii) 4-Methyl-2-methylenepentanoic acid

2 Carboxy-4-methyl-2-[(dimethylamino)methyl]pentanoic acid (57.3 g) is suspended melted at 140°–145° C. in an oil bath, and held at this temperature until bubbling ceases. The melt is cooled, taken up in water and acidified with 10% hydrochloric acid. Extraction with hexane, drying and evaporation yields 30.5 g of the title compound.

(B) 2-[(Acetylthio)methyl]-4-methylpentanoic acid

4-Methyl-2-methylenepentanoic acid (6.8 g) is stirred with 5 ml of thiolacetic acid for about 16 hours. The reaction mixture is concentrated in vacuo until crystallization occurs, yielding 3.6 g of the title compound, melting point 42°–47° C.

(C) (±)-2-[(Acetylthio)methyl]-4-methyl-N-[2-(4-morpholinyl)ethyl]pentanamide

2-[(Acetylthio)methyl]-4-methylpentanoic acid (2.0 g) is dissolved in 40 ml of tetrahydrofuran (THF) and 1.0 g of triethylamine. This solution is cooled to −5° C. and ethyl chloroformate in 5 ml of THF is added dropwise. The reaction mixture is stirred at −5° C. for 20 minutes and then N-(2-aminoethyl)morpholine [1.3 g] in 20 ml of THF is added dropwise. It is stirred at 20° C. for 4 hours and stored at 0° C. for about 16 hours. Triethylamine hydrochloride is filtered off and the filtrate is concentrated in vacuo. This residue is dissolved in ether and washed once with aqueous $NaHCO_3$ and twice with water. The ether is dried with $MgSO_4$, filtered and concentrated in vacuo to yield 1.6 g of material. This is purified by dissolving 0.6 g in 2 ml of ether and placing it on top of a pad of alumina (activity II 10 g). The column is washed through with 250 ml of ether which is concentrated in vacuo. Product crystallizes and is washed with 1:5 ether-pentane. The remainder of the crude is seeded with a small crystal and then washed with 1:5 ether-pentane. Total yield is 1.0 g of the title compound, melting point 54°–59° C.

Calc. for $C_{15}H_{28}N_2O_3S$: C, 56.93; H, 8.92; N, 8.85 S, 10.13. Found: C, 56.76, H, 8.91; N, 9.10; S, 10.01.

EXAMPLE 2

(±)-2-[(Acetylthio)methyl]-4-methyl-N-[2-(1-piperidinyl)ethyl]pentanamide

A solution of (±)-2-[(acetylthio)methyl]-4-methylpentanoic acid in 40 ml of THF is cooled to 5° C., followed by the dropwise addition of triethylamine (1.0 g) in 5 ml of THF. This solution is cooled to −5° C. and ethyl chloroformate in 4 ml of THF is added dropwise at −5° to 0° C. It is stirred for 30 minutes and N-(2-aminoethyl)piperidine in 30 ml of THF is added dropwise. The reaction mixture is stirred at 20° C. for 4 hours and stored at 0° C. for about 16 hours. Triethylamine hydrochloride is filtered off and the filtrate is concentrated in vacuo. The residue is dissolved in ether and washed with aqueous $NaHCO_3$. Ether is dried with $MgSO_4$, filtered and concentrated in vacuo to yield 2.1 g of crude product. This crude is absorbed on a 20-g pad of alumina act II and washed through with ether to yield 1.4 g of product which crystallizes from pentane, melting point 47°–50° C.

Calc. for $C_{16}H_{30}N_2O_2S$: C, 61.11; H, 9.62; N, 8.91; S, 10.19. Found: C, 61.04; H, 9.82; N, 8.93; S, 9.91.

EXAMPLE 3

2-(Mercaptomethyl)-4-methyl-N-[2-(4-morpholinyl)ethyl]pentanamide (±)-2-[(Acetylthio)methyl]-4-methyl-N-[2-(4-morpholinyl)ethyl]pentanamide (0.6 g) is dissolved in 20 ml of 1:1 ethanol:water. The solution is saturated with argon and 2 ml of 47% $NH_4OH$ is added. This is stirred under argon for 2 hours at room temperature. The reaction mixture is concentrated in vacuo and lyophilized for about 16 hours. The residue is dissolved in ether and stirred with charcoal to decolorize the product, which is then filtered through diatomaceous earth and concentrated in vacuo. The oil is dried at 45° C. in vacuo for about 16 hours to yield analytical product.

Calc. for $C_{13}H_{26}N_2O_2S \cdot \frac{1}{4} H_2O$: C, 55.98; H, 9.58; N, 10.04; S, 11.49. Found: C, 55.78; H, 9.48; N, 10.33; S, 11.41.

EXAMPLE 4

2-(Mercaptomethyl)-4-methyl-N-[2-(1-piperidinyl)ethyl]pentanamide (±)-2-[(Acetylthio)methyl]-4-methyl-N-[2-(1-piperidinyl)ethyl]pentanamide (0.8 g) is dissolved in 3 ml of water and 5 ml of absolute ethanol. After this solution is purged with argon, 2 ml of 56% $NH_4OH$ is added and the reaction mixture is stirred at room temperature for 2.5 hours. It is first concentrated in vacuo to get rid of excess ammonia and ethanol and then lyophilized for about 16 hours. The dark brown oil is dissolved in ether and stirred with a scoop of charcoal for 20 minutes. It is filtered through Celite and concentrated in vacuo to yield an oil. Drying in vacuo for 4 hours at 40° C. yields the analytical product.

Calc. for $C_{14}H_{28}N_2OS \cdot 0.25\ H_2O$; C, 60.72; H, 10.37; N, 10.12; S, 11.58. Found: C, 60.52; H, 10.38; N, 10.51; S, 11.20.

EXAMPLES 5–7

Following the procedure of Example 2, but substituting the compound listed in column I for N-(2-aminoethyl)piperidine, yields the compound listed in column II

| | Column I | Column II |
|---|---|---|
| 5 | N-(3-aminopropyl)-piperazinyl | (±)-2-[(acetylthio)methyl]-4-methyl-N-[3-(1-piperazinyl)propyl]pentanamide |
| 6 | 1-(4-aminobutyl)-4-methyl-piperazinyl | (±)-2-[(acetylthio)methyl]-4-methyl-N-[4-(4-methyl-1-piperazinyl)butyl]pentanamide |
| 7 | N-(2-aminoethyl)pyrrolidinyl | (±)-2-[(acetylthio)methyl]-4-methyl-N-[2-(1-pyrrolidinyl)ethyl]pentanamide |

EXAMPLE 8

3-(Acetylthio)-N-[2-(1-piperidinyl)ethyl]-2-(phenylmethyl)propionamide (A)

2-Carboxyl-3-(dimethylamino)-2-(phenylmethyl)propionic acid

Benzyl malonic acid (13 g) is mixed with 7.6 g of 40% aqueous dimethylamine and 5.4 g of 37% formalin in 150 ml of water. After 2 hours, the resulting solid is filtered, washed with water and partially dried in air to yield 20.8 g of material.

(B) Benzylacrylic acid

The above material is melted in a 170° C. oil bath and heated for 10 minutes, until amine evolution stops and bubbling has virtually ceased. The cooled product, a mobile liquid, is acidified with 10% potassium bisulfate, extracted with hexane, dried ($Na_2SO_4$) and evaporated to give 6.3 g of solid. The aqueous filtrates from the Mannich reaction of part A are allowed to stand for about 16 hours and then heated at 100° C. on a steam cone until bubbling ceases. Cooling, acidification and extraction as above give an additional 1.2 g of solid for a total yield of 7.5 g of benzyl acrylic acid.

(C) 3-(Acetylthio)-2-(phenylmethyl)propionic acid

Following the procedure of Example 1B, but substituting benzylacrylic acid for 4-methyl-2-methylenepentanoic acid, yields the title compound.

(D)

3-(Acetylthio)-N-[2-(1-piperidinyl)ethyl]-2-(phenylmethyl)propionic acid

Following the procedure of Example 1C, but substituting 3-(acetylthio)-2-(phenylmethyl)propionic acid for 2-[(acetylthio)methyl]-4-methylpentanoic acid and N-(2-aminoethyl)piperidine for N-(2-aminoethyl)morpholine, yields the title compound.

EXAMPLE 9–11

Following the procedure of Example 8, but substituting the compound listed in column I for benzyl malonic acid and the compound listed in column II for N-(2-aminoethyl)morpholine, yields the compound listed in column III.

| | Column I | Column II | Column III |
|---|---|---|---|
| 9 | phenyl malonic acid | N-(20-aminoeicosyl)piperidine | 3-(acetylthio)-N-[20-(1-piperidinyl)eicosyl]-2-phenylpropionamide |
| 10 | cyclopropyl malonic acid | N-(aminomethyl)pyrrolidine | 3-(acetylthio)-N-[(1-pyrrolidinyl)methyl]-2-(cyclopropyl)propionamide. |
| 11 | cyclohexyl malonic acid | N-(10-aminodecyl)morpholine | 3-(acetylthio)-N-[10-(4-morpholinyl)decyl]-2-(cyclohexyl)propionamide. |

What is claimed is:

1. A compound having the formula

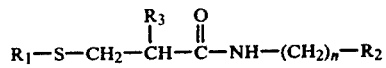

wherein
$R_1$ is hydrogen, alkanoyl of 2 to 10 carbon atoms or arylcarbonyl;
$R_2$ is 1-pyrrolidinyl, 1-piperidinyl, 4-morpholinyl, 1-piperazinyl, or 4-alkyl-1-piperazinyl;
$R_3$ is alkyl of 3 to 8 carbon atoms, cycloalkyl, aryl, or arylalkyl; and
n is an integer of 1 to 20.

2. A compound in accordance with claim 1 wherein $R_3$ is 2-methylpropyl.

3. A compound in accordance with claim 1 wherein $R_1$ is hydrogen, acetyl or benzoyl.

4. A compound in accordance with claim 1 wherein n is an integer of 2, 3 or 4.

5. The compound in accordance with claim 1 (±)-2-[(acetylthio)methyl]-4-methyl-N-[2-(4-morpholinyl)ethyl]pentanamide.

6. The compound in accordance with claim 1 (±)-2-[(acetylthio)methyl]-4-methyl-N-[2-(1-piperidinyl)ethyl]pentanamide.

7. The compound in accordance with claim 1 2-(mercaptomethyl)-4-methyl-N-[2-(4-morpholinyl)ethyl]pentanamide.

8. The compound in accordance with claim 1 2-(mercaptomethyl)-4-methyl-N-[2-(1-piperidinyl)ethyl]pentanamide.

9. A method for reducing the adverse effects of mammalian collagenase in a mammal host in need thereof, which comprises administering to said mammal an effective amount of a compound having the formula

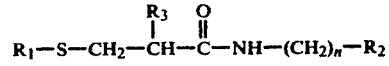

wherein
$R_1$ is hydrogen, alkanoyl of 2 to 10 carbon atoms or arylcarbonyl;
$R_2$ is 1-pyrrolidinyl, 1-piperidinyl, 4-morpholinyl, 1-piperazinyl, or 4-alkyl-1-piperazinyl;
$R_3$ is alkyl of 3 to 8 carbon atoms, cycloalkyl, aryl, or arylalkyl; and
n is an integer of 1 to 20.

10. A method in accordance with claim 9 wherein the mammalian host has rheumatoid arthritis.

* * * * *